United States Patent [19]

Yukihisa et al.

[11] Patent Number: 4,656,832
[45] Date of Patent: Apr. 14, 1987

[54] DETECTOR AND PARTICULATE DENSITY AND FILTER WITH DETECTOR FOR PARTICULATE DENSITY

[75] Inventors: Takeuchi Yukihisa, Chita; Miura Yasunao, Kasugai; Hirayama Tsukasa, Ohbu, all of Japan

[73] Assignee: Nippondenso Co., Ltd., Kariya, Japan

[21] Appl. No.: 871,146

[22] Filed: Jun. 3, 1986

Related U.S. Application Data

[63] Continuation of Ser. No. 536,389, Sep. 27, 1983, abandoned.

[30] Foreign Application Priority Data

Sep. 30, 1982 [JP] Japan .................. 57-171511
Apr. 21, 1983 [JP] Japan .................. 58-71013

[51] Int. Cl.$^4$ .................. F01N 3/02; B01D 46/24; G01R 27/02
[52] U.S. Cl. .................. 60/303; 55/283; 55/466; 55/DIG. 30; 60/311; 73/28; 324/65 R; 340/628
[58] Field of Search .................. 60/303, 311; 55/466, 55/283, DIG. 30; 73/28; 324/62, 64, 65 R, 65 P, 71.1; 340/620, 628

[56] References Cited

U.S. PATENT DOCUMENTS

| | | | |
|---|---|---|---|
| 4,158,610 | 6/1979 | Bauer | 73/28 |
| 4,283,207 | 8/1981 | Martyniuk | 55/523 |
| 4,404,795 | 9/1983 | Oishi | 55/466 |
| 4,427,418 | 1/1984 | Kogiso | 60/303 |
| 4,442,422 | 4/1984 | Murata | 324/65 R |

Primary Examiner—Douglas Hart
Attorney, Agent, or Firm—Cushman, Darby & Cushman

[57] ABSTRACT

A detector for particulate density and the filter for trapping particulates which includes the detector includes a heat resistant insulating member and a pair of electrodes disposed on or within the surface of the filter. When the conductive particulates are attached on the heat resistant insulating member, the resistance of the member is decreased, and reversely, when the particulates are burned away from the member, the resistance is increased. Therefore, by detecting the resistance variation, the particulate density can be measured accurately and the optimum timing to refresh the filter can be determined. The detector is heat resistive, and also can detect whether the filter is completely refreshed or not. The surface of the heat resistant insulating member may be formed to be irregular so that the particulates are easily attached to the member resulting in an increase in measurement precision. An electric heating means for heating particulates trapped on the filter, is mounted in the detector device in order to eliminate hydrocarbon and water content, thereby stabilizing the resistivity of the particulates. Consequently, detecting particulate density can be utilized more precisely. The controller employs a controlling unit for determining the timing to refresh the filter adequately, by receiving the signals of vehicle conditions such as the particulate density.

5 Claims, 23 Drawing Figures

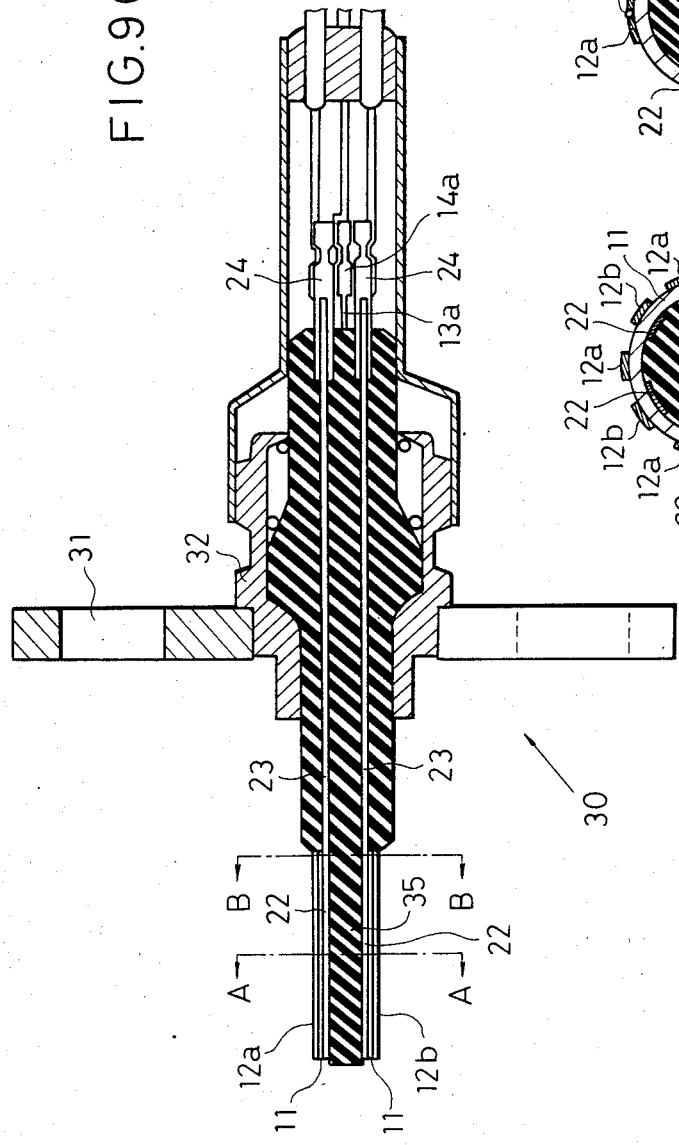
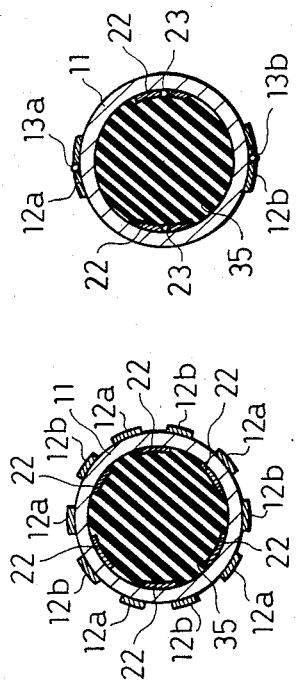

DETECTOR AND PARTICULATE DENSITY AND FILTER WITH DETECTOR FOR PARTICULATE DENSITY

This is a continuation of application Ser. No. 536,389, filed Sept. 27, 1983 which was abandoned upon the filing hereof.

BACKGROUND OF THE INVENTION

1. Field of the Invention

This invention relates to a detector for particulate density of engine exhaust gases and a filter including the detector for particulate density.

2. Description of the Prior Art

Given below is a description of equipment which traps particulates in exhaust gases of a diesel engine, and a conventional method for measuring the density of particulate trapped by the filter element which is mounted in the equipment for trapping particulates.

FIG. 1 shows an example of equipment for trapping particulates. The trapping equipment A is connected to a combustion engine, particularly to an exhaust-collector ring 2 of a diesel engine. This equipment is provided with a metallic case 3 containing an inlet port 3a connected to the exhaust-collector ring 2 and an outlet port 3b for discharging exhaust gases. The case 3 includes therein a filter 4 for trapping particulates and a heater 5 attached in a concave within the filter. The heater 5 burns the particulates trapped on the surface of the filter 4 so as to refresh the filter. The current supplied from the battery 6 to the heater 5 is controlled by a controller 7. The controller 7, receives a signal from a differential pressure sensor 8 which measures the pressure loss due to the filter 4, and receives a signal from a rotating velocity sensor 9 which detects the rotating velocity of the engine.

The exhaust gases discharged from the engine 1 flow into the case 3 of the trapping equipment A through the inlet port 3a, passing through the filter 4, and thereafter flow out through the outlet port 3b. When exhaust gases are passing through the filter 4, particulates included in the gases are eliminated by being trapped on the surface of the filter 4. At the time when a certain amount of particulates are collected and the air-flow resistance of the filter 4 increases, the differential pressure sensor 8 sends out a signal corresponding to the pressure loss. The differential pressure between an upstream side and a downstream side of the filter, which is detected by the differential pressure sensor, varies also depending on the rotating velocity of the engine. Thus, both signals from the differential pressure sensor 8 and from the rotating velocity sensor 9 are inputted to the controller 7, so that the controller 7 calculates the effective air-flow resistance, that is the air-flow resistance only depending on the density of trapped particulates. When such effective resistance reaches a predetermined value, the controller 7 begins supplying electric current to the heater 5. Thereby, the heater 5 heats up to the temperatures at which particulates (mainly composed of carbon) can be burned.

The particulates are heated and burned by the heater 5. The burning starts close to where the heater is mounted, and expands towards the up-stream side of the exhaust gases. At the same time, the heat is transmitted towards the down-stream side along with the exhaust gas flowing so that the burning effectively expands towards the down-stream side of the exhaust gases. Therefore, mounting the heater at the place where the particulate density is maximum, adjacent to the upstream side end surface, can cause the easier ignition and effective expansion of the burning through the filter so as to burn out all of the trapped particulates.

When the air-flow resistance decreases to the predetermined value because the particulates are burned away, the current supplied to the heater 5 is cut off and the filter 4 is finished being refreshed.

The timing to refresh the aforesaid filter 4 is important for the reason explained in the following.

The particulates trapped on the filter are ignited and burned to refresh the filter so as to reproduce an original mesh structure. If the density of the particulates trapped on the filter are more than a certain value, the particulates will burn excessively at a high combustion temperature so that the filter will be melted and broken. On the contrary, if the density of the particulates trapped on the filter is less than a certain value, the particulates will burn insufficiently so that the filter will not be refreshed enough. Therefore, the optimum range of the density of the trapped particulates is limited in order to cause an optimum burning. It is important to ignite and burn the particulates when the density of trapped particulates is within such an optimum range. For this purpose, the density of the trapped particulates should be measured accurately so that the current may be timely flowed to the heater when the density reaches to a predetermined value, whereby the filter is ignited and burned in order to be refreshed.

However, the conventional methods for detecting the differential pressure of the exhaust gases between both sides of the filter, have not measured the exact density of the trapped particulates.

This is because the differential pressure of the exhaust gases between both sides of the filter depends also upon the flow velocity of the exhaust gas. In order to calculate such a flow velocity of the exhaust gas, the rotating velocity of an engine and the temperature of the exhaust gas, or the negative pressure of the intake manifold should also be detected, therefore a large sized equipment is required.

In addition, such a method has a disadvantage in that the predicting error is inevitably larger in value due to calculation by using a lot of unknown parameters.

Another conventional method for detecting the density of the particulates trapped on the filter, is to calculate roughly from the total consumption of fuel. This method is adequate for calculating the approximate estimate, but errors are too large to solve the aforesaid problem.

SUMMARY OF THE INVENTION

One object of the present invention is to provide a detector which directly detects the density of the particulates trapped on the filter.

Another object of the present invention is to prevent the filter from melting by adequately controlling the timing required to burn and refresh the filter.

A further object of the present invention is to keep the trapping efficiency of the filter high by detecting the particulate density by the detector thereby controlling the timing required to burn and refresh the filter.

Still another object of the present invention is to provide the filter with a detector therein which can directly detect the density of the particulates within the filter and more easily control the timing required to burn and refresh the filter.

Still another object of the present invention is to provide a detector which can stabilize the resistivity of the particulates by heating the particulates to eliminate hydrocarbon and water content from them which cause instability in the resistivity, and which can exactly detect the density of the particulates trapped on the detector.

The present invention uses a heat resistant insulating member placed in the passage of the exhaust gases, and measures the density of the particulates adhering or absorbed on the heat resistant insulating member. The inventors have noticed that the particulates are generally composed of carbon particulates which are conductive. The density is calculated by making use of the fact that an insulating member reduces its resistance due to adhered or absorbed conductive particulates. The inventors have measured the density of trapped particulates by detecting the resistance.

The main ingredient of the particulates is carbon, and other minor components are such as hydrocarbon, ash content and water content. The component ratio of the minor components is variable in accordance with the engine conditions or the running state of the vehicle. Carbon is a semiconductor, and on the other hand, hydrocarbon is an insulator and water has complicated conduction characteristics, so that the resistance characteristics of the whole particulate varies complexly, in accordance with temperature, pressure and time.

Therefore, it is necessary to stabilize the resistivity of the particulates so as to determine the particulate density by detecting the resistivity. Accordingly, this invention also provides a detector which stabilizes the resistivity and can detect the exact particulate density.

BRIEF DESCRIPTION OF THE DRAWINGS

By way of example and to make the description more clear, reference is made to the accompanying drawings in which;

FIG. 2 shows the structure of the detector for particulate density according to the first embodiment: FIG. 9(a) is a longitudinal sectional view of the whole detecting device mounted with the detector for particulate density according to the sixth embodiment, FIG. 9(a) is a cross-sectional view taken along the line A—A of the FIG. 9(a), FIG. 9(c) is a cross-sectional view taken along the line B—B of FIG. 9(a)

DETAILED DESCRIPTION OF THE INVENTION

Figure 1:
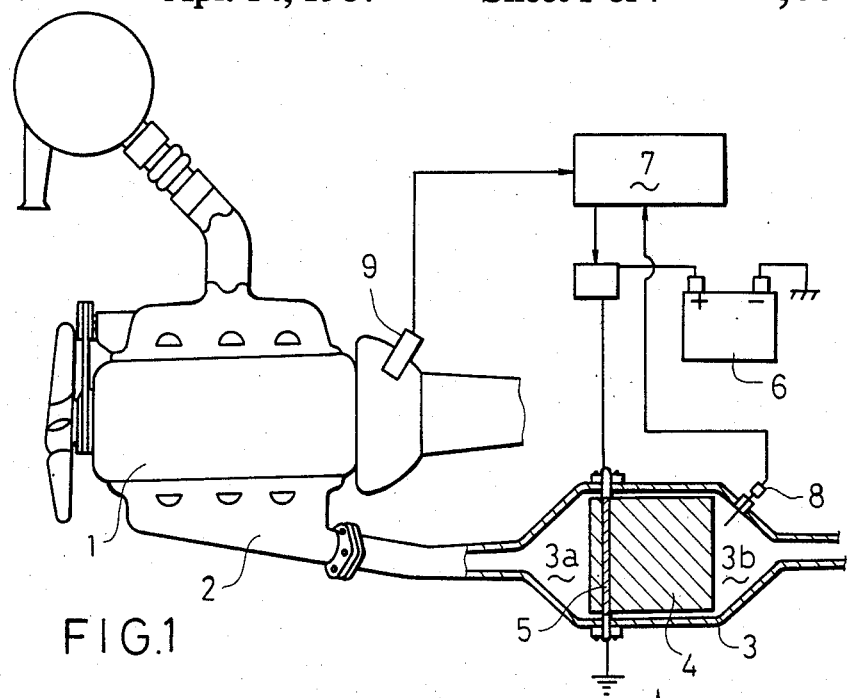
FIG. 1 shows the general structure of the whole trapping equipment with a capacity for refreshing and the system for controlling the timing to refresh the filter.

A first feature of the present invention is a detector for particulate density which comprises;

a heat resistant insulting member for trapping conductive particulates and a pair of electrodes for detecting the resistance of the insulating member which are disposed opposite to each other in the heat resistant insulating member.

The inventors have also noticed that this detector for particulate density does not always have to be disposed solely outside of the filter. The detecting portion which is the same as the above mentioned detector can be placed also within or on the surface of the filter, or the detecting portion can be formed integrally of the same material with that of the filter as a part of the filter. Thereby, the particulate density within the filter can be detected more directly and accurately.

Accordingly, a second feature of the present invention is comprised of a filter which includes;

a detecting portion for particulate density comprising a heat resistant insulating member for trapping conductive particulates and a pair of electrode for detecting the resistance of the insulating member which are disposed opposite to each other in the insulating member.

A third feature of the present invention is comprised of a detector for particulate density which comprises;

a heat resistant insulating member for trapping conductive particles;

at least a pair of electrodes for detecting the resistance of the heat resistant insulating member which are disposed opposite to each other on the insulating member and at least one electric heating means for heating the trapped particulates on the insulating member.

In this description, the conductive particulates are mainly composed of carbon. The substrate of the detector should be formed of a heat resistant insulating member in order to prevent the detector from being melted by combustion heat when the filter is burned to be refreshed. That is, the detector is required to be heat resistant at a higher temperature than the burning temperature of the particulates.

The substrate of the detector should also be formed of an insulating member in order to improve its sensitivity for detecting particulate density. This is because the insulating member shows a high value of resistance without carbon particulates, and shows an extremely lower value of resistance as the amount of carbon particulates attached to the substrate increases. It is preferable for the substrate of the detector to have a high sensitivity.

Therefore, the heat resistant insulating member should be made of ceramics having both heat resisting and insulating properties.

Methods for trapping conductive particulates using the heat resistant insulating member according to the present invention are described below. The first method is to trap the particulates by attaching them to the surface of the heat resistant insulating member. The second method is to form the whole detector of porous ceramics and trap the particulates within the porous ceramics. Then, the variation in resistance may be measured in order to detect the density of the trapped particulates, on the surface of or within the member. A pair of electrodes may be disposed on the surface of the heat resistant insulating member, in the first method, and may be disposed opposite to each other within the detector, in the second method.

The detector for particulate density described above may be situated adjacent to the aforesaid filter, such as on the upstream or downstream side of the filter.

According to the first feature of the invention, the method of measuring, by the detector for the particulate density, should be carried out on the assumption that the density of the trapped conductive particulates within the detector is in proportion to that of the trapped particulates within the filter. Therefore, in fact, there are some errors. The inventors have disposed the detecting portion for particulate density within or on the surface of the filter, or disposed at least a pair of opposite electrodes in a part of the filter to form the detecting portion as one part of the filter. This makes it possible to detect the density of the particulates trapped within the filter, extremely accurately and directly.

The embodiments of the present invention will be described in greater detail below.

DETAILED DESCRIPTION OF THE PREFERRED EMBODIMENTS

The structure of the detector for particulate density is shown in FIG. 2 according to the first embodiment.

Figures 2A, 2B:
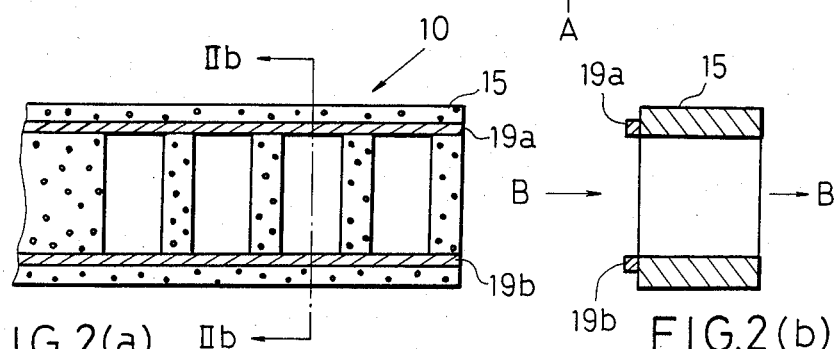
FIG. 2(a) is a front elevation of the detector.
FIG. 2(b) is a cross-sectional view taken along the line IIb—IIb of FIG. 2(a) and FIG. 2(c) is a perspective illustration of the detector.

FIG. 2(a) is a front elevation. FIG. 2(b) is a cross sectional view taken along the line IIb—IIb in FIG. 2(a) and FIG. 2(c) is a perspective view.

The detector 10 for particulate density is comprised of the heat resistant insulating member 15 having a lattice like structure and the conductive electrodes 19 attached on the surface of the member 15 shown by cross hatched lines.

Figure 2C:
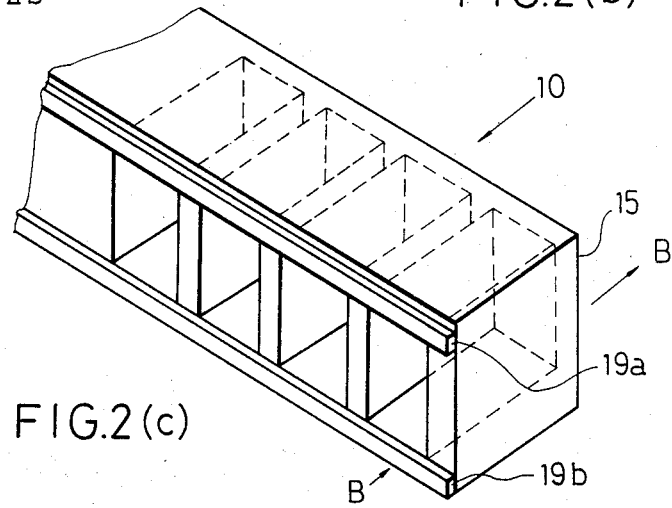

In FIG. 2(c), the arrow B designates the direction of air-flow of the exhaust gases. The particulates included in the exhaust gases attach to the surface of the aforesaid heat resistant insulating member 15 having lattice structure, thereby the resistance between both electrodes 19a and 19b is varied. Accordingly, measurement of this resistance can determine the amount of the attached particulates.

Figure 3:
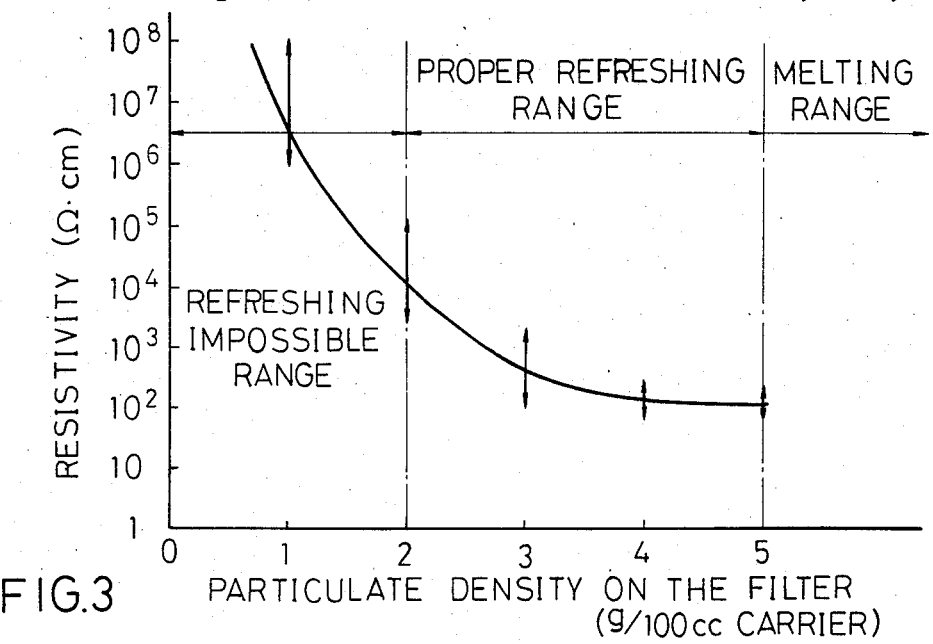
FIG. 3 is a graph showing the relationship between the density of carbon trapped on the filter and the resistivity detected by the detector according to the first embodiment.

In FIG. 3, the abscissa shows the weight of the trapped particulates within the filter, per 100 cc carrier, and the ordinate shows the resistivity calculated from the resistance measured by the detector for particulate density according to the present embodiment. As apparent from FIG. 3, the resistivity decreases corresponding to the weight increase of the trapped particulates, in proportion to the expoential function of the reciprocal weight. When the particulate density is below 2 g/100 cc filter volume (hereafter, "2 g/100 cc filter volume" is abbreviated as "2 g"), the amount of trapped particulates is so small that burning cannot be sufficiently transmitted. Therefore, the filter cannot be burned on the downstream side. On the contrary, when the particulate density is above 5 g and the heater is turned on to refresh the filter, the amount of the trapped particulates is excessive so that the combustion temperature reaches more than 1400° C. and in result, the filter is melted. Accordingly, when the particulate density reaches more than 5 g, the timing to ignite is too late, and when the particulate density is below 2 g, the timing to ignite is too early, as was ascertained by experiment. Thus, the adequate range of density is limited between 2 g and 5 g to refresh the filter. In this case, when the resistivity detected by the detector for particulate density becomes below $10^4$ $\Omega$cm, the ignition must be done. And when the resistivity becomes below $10^2$ $\Omega$cm, the filter is possibly melted. Thus described, the particulate density within the filter can be detected by measuring the resistance variation caused by carbon attached to the detector for particulate density.

When various filters for trapping particulates are practically used, such filters and the detectors are each placed at the position where they are usually used, and then the characteristic curve of the relation between resistivity and particulate density is practically measured. From such experimental values, the timing to ignite and refresh can be determined as described above.

Figure 4A:
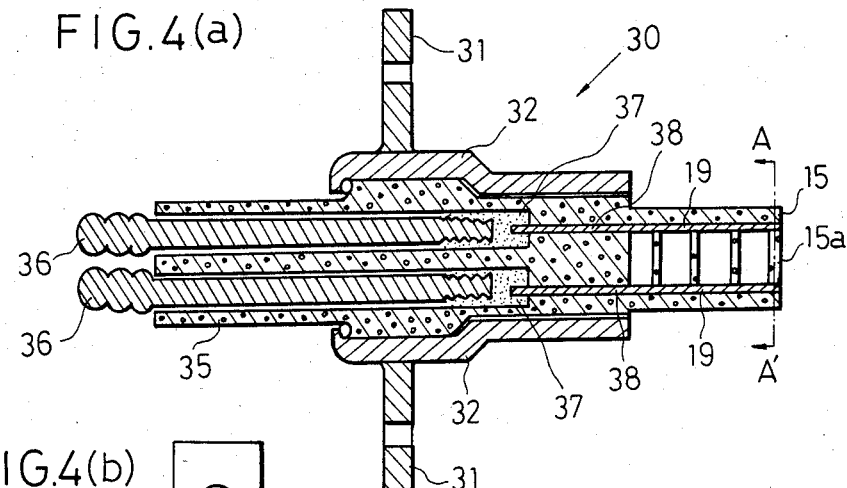
FIG. 4(a) is a longitudinal sectional view of the whole detecting device for particulate density mounted with the detector.

FIG. 4(a) is a longitudinal sectional view of the detecting device 30 which is mounted with the aforesaid detector 10 for particulate density.

Figure 4B:
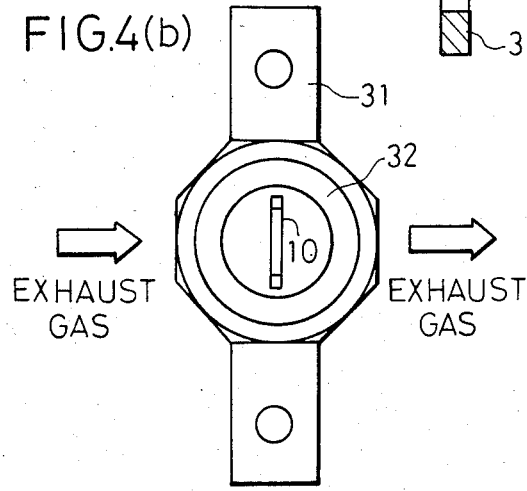
FIG. 4(b) is a plan view of the same detecting device as shown in FIG. 4(a)

FIG. 4(b) is a plan view. The heat resistant insulating member 15 which is a component of the detector 10 for particulate density is integrally fixed to the insulator 35. The electrodes 19 attached on the heat resistant insulating member 15 (hereafter, also designated as "substrate") are connected to a lead wire 38, then the lead wire 38 is connected to a pair of external terminals 36, and the resistance is measured from the terminals 36. The electrode 19 and the lead wire 38 should be formed of heat resistant material, such as heat resistant conductive material composed of nickel-platinum. The lead wire 38 and the external terminal 36 are connected by the conductive powder 37 which seals the exhaust gases. The insulator 35 is mounted within a metallic housing 32. The housing 32 has a flange 31, and the flange 31 is fixed to a filter case 3 (shown in FIG. 1). The resistance can be measured from the external terminals 36 which extend out of the filter case 3.

Next, the producing method of the detecting device for particulate density will be explained in the following.

Cordierite ceramics powder and organic binder are mixed together and then formed in the aforesaid lattice like suructure by certain molding. On this molded substrate, a platinum wire of 0.1-0.2 $\phi$mm is adhered or a paste of platinum is printed of 0.01-2 mm thick, thereafter they are sintered at 1300°-1400° C. for 2-5 hours. Then on this sintered material, slurry mainly composed of $\gamma$-$Al_2O_3$ is attached and sintered at 1000°-1200° C. for 1-2 hours so as to form an extremely irregular surface between the electrodes. It is to increase the particulates attached on the surface that the surface between the electrodes is formed to be irregular. In this way, the detector with the specific surface area of 1-600 $m^2/g$ can be formed. When the specific surface area is below 1 $m^2/g$, the attached particulates are scattered by the exhaust gas flow so that the error of density measurement is more than 40% resulting in inferior measurement precision. When the specific surface area is above 1 $m^2/g$, the attached particulates are prevented from scattering.

Accordingly, it was ascertained that the specific surface area is desired to be more than 10 $m^2/g$ in order to improve the measuring precision.

Codierite is employed in the present embodiment, as the heat resistant insulating member, but other ceramics, one of them alone or a mixture of them, can also be employed for the material such as alumina, silica, magnesia, zirconia, silicon nitride-titanate, $Fe_2O_3$, Kaolin, and talc. As the material for the electrodes, nickel wire or Fe-Cr-Al wire can also be employed.

In the present embodiment, the resistivity on the surface of the substrate is measured so that the electrodes are preferred to be disposed on the surface of the substrate. However, a part of the eletrode may be reasonablly disposed within the ceramics substrate.

The second embodiment of the detector for the particulate density will be described in the following.

Figure 5:
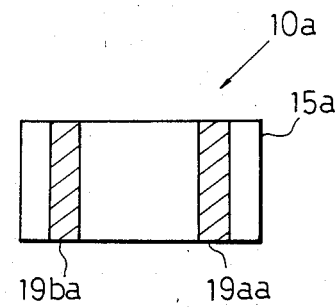
FIG. 5 is a plan view of the detector according to the second embodiment.

FIG. 5 shows the structure of the detector for the particulate density according to the second embodiment. The substrate to be attached with particulates is formed in the shape of a plate, and on the surface of the substrate are metalized the electrodes 19ba, 19aa which are opposite each other in line. In this case, it should be prevented to disturb the exhaust gas flow. For this reason, the dimension of the detector should be limited, such as below a 15 mm square, or below 20 mm in diameter. In the present embodiment, on the surface of the substrate of a 15 mm square with thickness of 1-2 mm, platinum wire of 0.1-1 mm in diameter is placed, thereafter they are molded together by pressing, sintered at 1300°-1450° C. for 2-5 hours, attached with $\gamma$-$Al_2O_3$, sintered again, and the resulted detector is mounted as explained above.

The third embodiment will be then described in the following.

In this embodiment, after sintering the heat resistant insulating member 15 of a lattice structure which constitutes the detector according to the first embodiment, additional arrangement is made to form more irregular surface on the insulating member.

On the lattice structured surface of the first embodiment, is printed paste containing Pt (or Fe-Cr-Al, Ni-Cr, Ni), then sintered at 900°-1300° C. for 1-2 hours to form electrodes. Next, it is placed within a high temperature furnace wherein such gases as $Si(CH_3)Cl_3$, $SiH_4+CH_4$ can flow in 10-100 cc/minute, and wiskers composed of SiC are formed on the surface of the detector. Thus the detector with specific surface area of more than 10 $m^2/g$ can be formed. The detector of the present embodiment was compared with those of the first and second embodiment by measuring the resistivity under the same conditions. Consequently, it was proved that scattering of the particulate of this embodiment was less than that of the other embodiments, and the error of the detected density of the particulates trapped on the filter was below 10%. The wisker is composed of SiC in this embodiment, but the wisker can be also composed of other heat resistant material such as $Si_3N_4$, $TiO_2$, $Al_2O_3$, $SiO_2$, $ZrO_2$, MgO, WC, TiC and TiN by CVD.

Such a detector is preferred to be disposed in the downstream side of gas-flow within 100 mm from the end face of the filter because the detector should be also be burned, when the filter is ignited and refreshed, in order to burn away the attached particulates on the detector.

Figure 6:
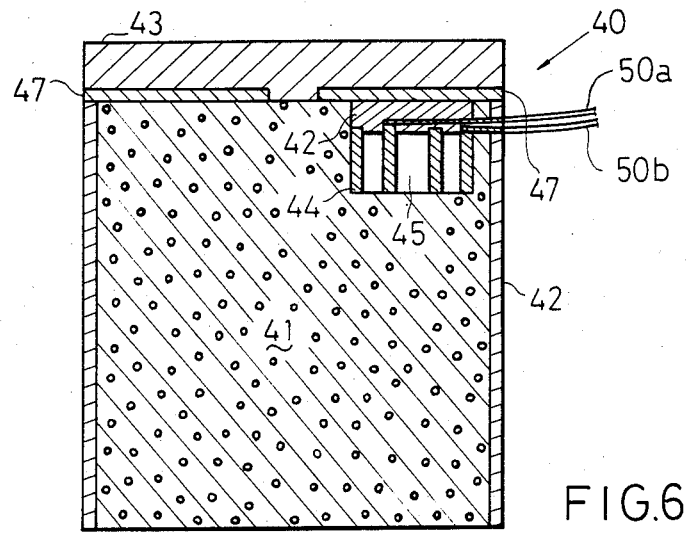
FIG. 6 is a schematic cross-sectional view of the filter for trapping particulates including the detecting portion for particulate density according to the fourth embodiment.
Figure 7A:
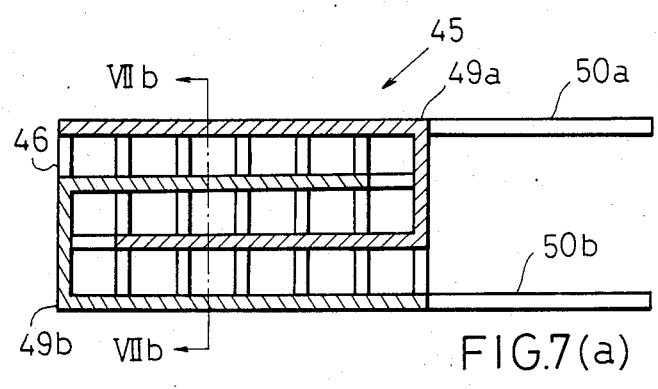
FIG. 7(a) is a schematic cross-sectional view of the detecting portion for the particulate density involved in the filter shown in FIG. 6.
Figure 7B:
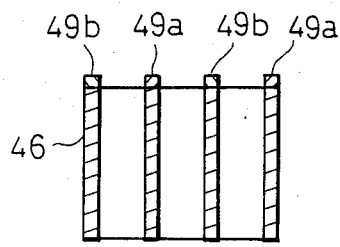
FIG. 7(b) is a cross-sectional view taken along the line VIIb—VIIb of FIG. 7(a)

The the filter according to the fourth embodiment will now be described, which includes the detecting part of the same structure as of the aforesaid embodiment. FIG. 6 shows the first embodiment of the filter. On the upper side end of the filter body 41 composed of the porous ceramics, is disposed a heater 47 to ignite and burn the filter. And a sealing member 43 of ceramics is placed to seal the heater. On a part of the upper side end of the filter body 41, a concave portion 44, to set the detector for particulate density, is formed, and the detecting part 45 is fitted in the concave portion 44. As shown in FIG. 7, comb like electrodes 49a and 49b are placed on the surface of the lattice substrate. The decrease of the resistance is measured, which is caused by the attached particulates on the surface of the substrate. The lead wires 50a, 50b at both ends of the detector are connected to the power source through a resistance detector for detecting the resistance from the variation in current, the output from the resistance detector is coupled to the controller 7. The controller 7 controls the power supplied to the heater 47 to burn the filter when the resistance decreases to a predetermined value.

On burning, the particulates attached on the detecting part are burned together, so that the resistance is increased. Therefore, when the resistance increases to another predetermined value, the heater may at this time be turned off. To be more specific, when the density of the attached particulates on the surface of the porous substrate is more than 2 g/100 cc carrier, the current is controlled to flow through the heater so as to refresh the filter. In the other words, when the resistance detected by the detecting part decreases to below $10^4$ $\Omega$cm, the current is controlled to flow. Moreover, after refreshing, the resistance increases to above $10^9$ $\Omega$cm, therefore detecting the resistance of the detecting part enables one to detect if the filter is certainly refreshed or not.

When the precission of this detecting was tested by experimental running of LA#4 mode, the measurement error about the particulate density in this method was 10-15%, and that about detecting whether refreshed completely or not, was below 5%.

In this manner, the detecting for particulate density of further higher precission compared with the prior arts can be provided.

The producing method of the filter including the detecting part for particulate density, according to the present invention will be detailed in the following.

Ceramics clay mainly composed of Cordierite is formed, then shaped into the substrate 46 by pressing which has through holes in the lattice structure. On the surface of the substrate, the electrodes are placed. The paste mainly composed of Pt, Ni, Ni-Cr or Fe-Cr-Al is printed in thickness of 0.01-2 mm, to form electrodes at constant intervals, thereafter dried at 100°-200° C. for 1-2 hours. Thereon, slurry containing $\gamma$-$Al_2O_3$ is deposited and dried at 100°-200° C. for 1-2 hours to result in a detecting part for particulate density before sintered.

Then an organic substance having a three dimensional mesh structure (such as urethane form and polyvinyl form) is shaped in a circular cylinder of 120 mm in diameter and 150 mm height. Such substance should have 8-20 cells at 1 inch. At the upper side end surface of the cylinder, a fitting concave portion 44 is formed wherein the aforesaid detecting part can be disposed. This cylinder is immersed into slurry containing 50-150 weight parts of cordierite, 1-20 weight parts of organic binder (such as polyvinyl alcohol, methyl cellulose, and ethyl cellulose), and 200-300 weight parts of water. Then the excessive slurry is eliminated by a centrifugal separator and a roll extruding machine, and the product is dried at 100°-200° C. for 1-2 hours. Around this dried material, another organic substance having a three dimensional mesh structure is positioned, the substance has a 30-50 mesh at 1 inch and has been impregnated with ceramics slurry, thereafter it is dried at 100°-200° C. for 1-2 hours to form reinforcing wall 42.

The aforesaid honeycomb detecting port for particulate density which is not sintered, is disposed within the fitting concave portion 44. At the upper end face of the detecting part, the organic substance forming the three dimensional mesh structure 42 is placed which is 8-20 mesh at 1 inch and impregnated with ceramics slurry. This makes the upstream side surface of the detecting part 45 flat. On this upstream side surface of the filter, the heater 47 mainly composed of Fe-Cr-Al is disposed. And thereon, the organic substance having a three dimensional mesh structure is placed, which has been impregnated with the ceramics slurry without drying and which will form ceramics sealing member 43 after being sintered.

The filter including the detecting part for particulate density which is fitted as explained above, is then dried at 100°-200° C. for 1-2 hours. And the lead wire are brazed to the electrodes of the detecting part by vacuum brazing. The brazing material is preferred to contain heat resistant material such as Pt, Pb.

Next, the fifth embodiment will be described below.

Figure 8A:
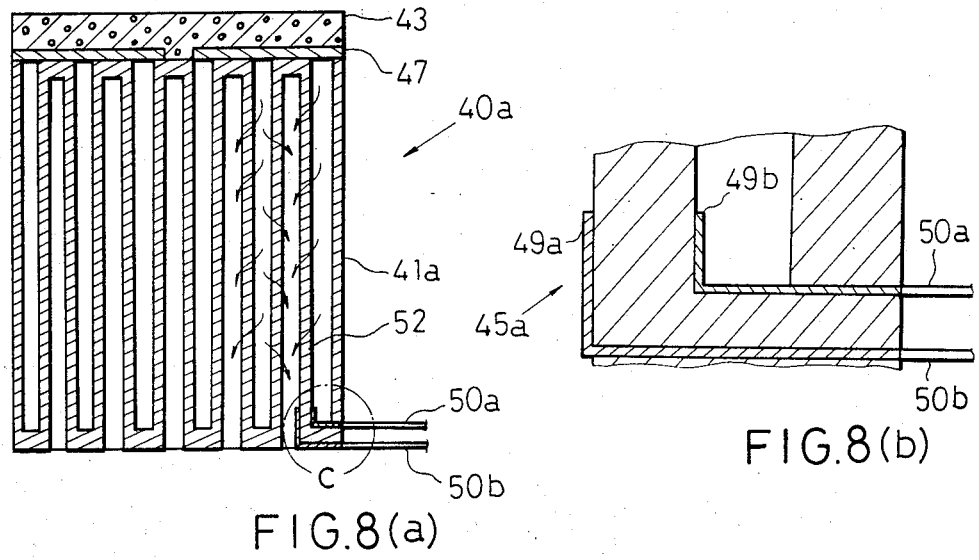
FIG. 8(a) is a schematic cross-sectional view of the filter for trapping particulates according to the fifth embodiment.
Figure 8B:
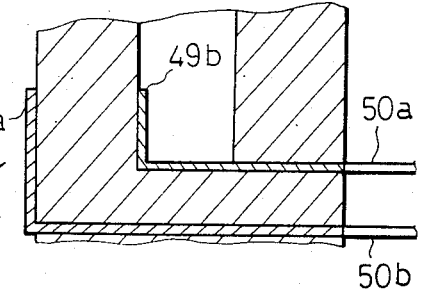
FIG. 8(b) is a partially enlarged view of the detecting portion for particulate density involved in the filter of FIG. 8(a)

FIG. 8 shows the structure of the filter according to the fifth embodiment. FIG. 8(a) is a cross-sectional view and FIG. 8(b) is an enlarged view of the detecting part for particulate density shown as C in FIG. 8(a). In this embodiment, a pair of electrodes 49a, 49b are disposed opposite to each other on the surface of the partition wall 52 which has a honeycomb structure and is composed of porous ceramics, then the resulting detector for particulate density 45 is placed at the downstream side of the filter. Therefore, the particulates trapped on the honeycomb structure of the partition wall act to vary the resistance between the electrodes. Accordingly by detecting this resistance, refreshing of the filter can be controlled similarly to the fourth embodiment. This embodiment has a feature that it can be precisely detected whether the filter is refreshed certainly to the end of downstream side, because the detector for particulate density is situated at the downstream side. The detecting error about the particulate density in the embodiment is not so different from that of the fourth embodiment. But the error about detecting whether the filter is refreshed to the downstream end or not, is 5-8%.

The producing method of the filter according to the fifth embodiment will be explained hereafter.

In the mold of the honeycomb structure as shown in FIG. 8(a), firstly the lead wires for electrodes are placed in the detecting part 45a, then the main ingredients of isocyanate and polyol added with foaming agent and polymerization catalyst, are mixed and stirred, thereafter the resulting liquid is flowed into the mold to foam within it. After it is taken out of the mold, it is heated at 80° C. for 1 hour to be solidified. Then the thin films formed on the bubbles are processed by alkali extraction and removed by explosion removal of film.

This material is immersed into ceramics slurry similarly to the fourth embodiment, and the excessive slurry is eliminated by such as a centrifugal separator and a roll extruding machine. Thereafter it is dried at 100°-200° C. for 1-2 hours. The platinum wires are placed on the surface of the dried material at the upstream side so as to form a heater 47. Other wires such as nickel-chrome wire or iron-chrome aluminum wire can also be employed for the heater. Further thereon, is placed an organic substance having a three dimensional mesh structure impregnated with ceramics slurry, which is dried at 100°-200° C. for 1-2 hours thereafter sintered at 1300°-1450° C. for 2-5 hours to complete the filter.

The sixth embodiment will be explained next below.

FIG. 9(a) is a longitudinal sectional view of a detecting device 30 mounting a detector for particulate density according to the sixth embodiment, FIG. 9(b) is a cross-sectional view taken along the line A—A of FIG. 9(a), and FIG. 9(c) is a cross-sectional view taken along the line B—B of FIG. 9(a).

Figure 10A:
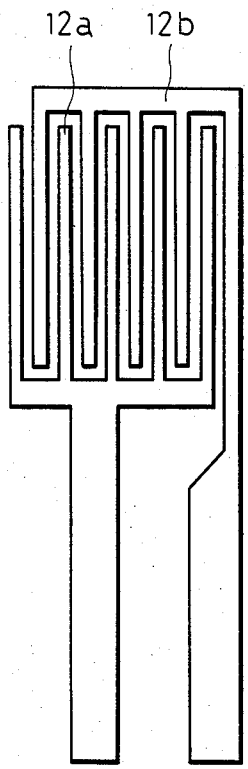
FIG. 10(a) is a pattern view of the electrode for detecting the particulate density.
Figure 10B:
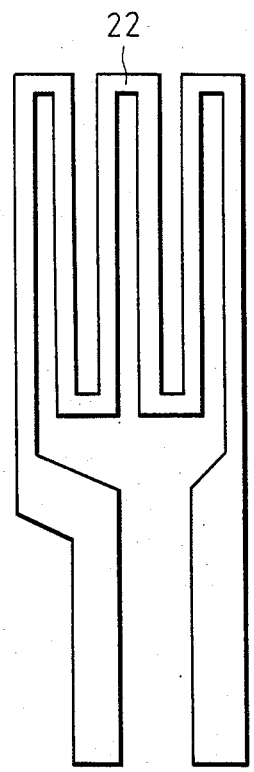
FIG. 10(b) is a pattern view of the electric heating means for heating particulates.
Figure 11:
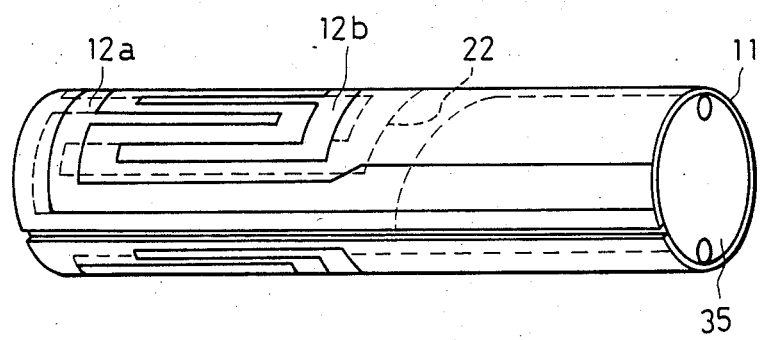
FIG. 11 is a perspective schematic illustration of the essential portion of the detecting device for particulate density.

The heat resistant insulating member 11 (hereafter only designated as "substrate") comprises a part of the detecting device for particulate density 30. The substrate 11 is connected integrally to the insulator 35. On the surface of the substrate 11, the electrodes 12a, 12b for detecting particulate density are formed by printing paste and the like, as shown in FIG. 10(a). An electric heating means 22 for heating particulates is disposed between the substrate and the insulator 35 as shown in FIG. 10(b). The main structure of the detecting equipment (i.e. the detecting part for the particulate density) is shown in FIG. 11 which is a perspective view. The electrode 12a is connected to the external terminal 14a through the lead wire 13a. The resistance is detected from the external terminal 14a.

The electric heating means 22 for heating particulates is connected to the external terminals 24 through lead wire 23. The insulator 35 is mounted within the metallic housing 32. The housing 32 has a flange 31 which is connected to the filter case 3 and from the external terminals 14a, 14b, the resistance is measured.

Figure 12:
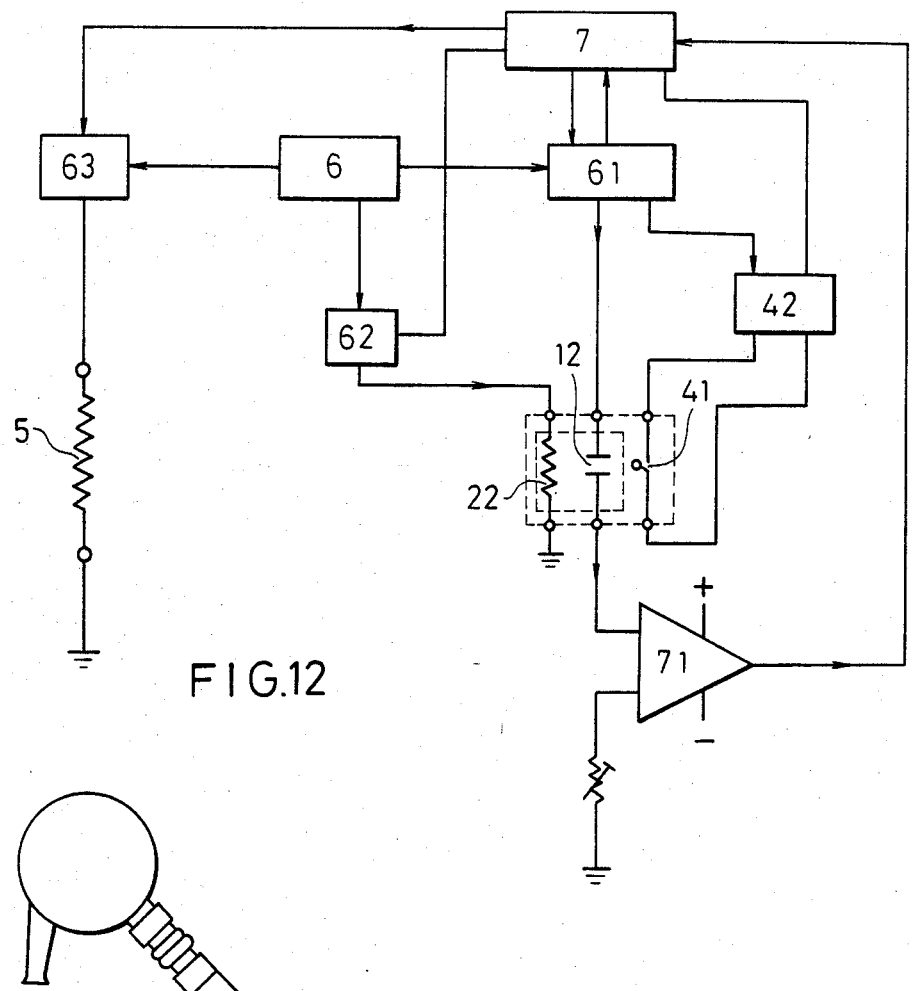
FIG. 12 is a circuit diagram showing one example of the controller with the detector for refreshing the filter.
Figure 13:
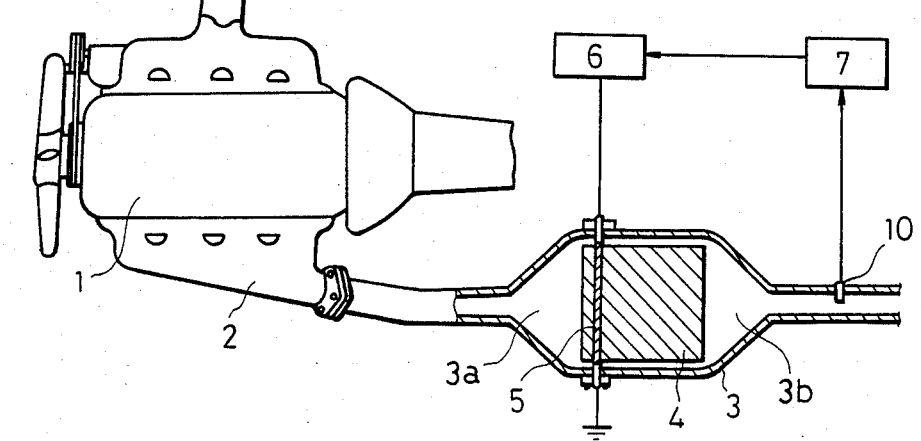
FIG. 13 shows the whole structure of the trapping equipment for particulates employing the detector for particulate density according to the sixth embodiment, and FIG. 14 and FIG. 15 respectively shows the seventh embodiment.

FIG. 12 shows one example of the controlling method for refreshing the filter using the detecting device for the particulate density. FIG. 13 shows one example of the system wherein the detecting device for particulate density is practically mounted on the vehicle.

The place to mount the detecting device can be near the engine or on the case of the filter, other than shown in the example.

In FIG. 12, the controller is comprised of;

electrodes 12 for detecting particulate density, an electric heating means 22 for heating particulates, a temperature detector 41, a controller 42 for the temperature detector, a heater 5 for refreshing the filter, a power source 6, a constact voltage power source 61, a power source 62 for the heater to heat particulates, a resistance detector 71 and a central controlling unit 7.

The controlling method will be explained below.

The central controlling unit 7 controls the output power of the electric heating means 22 by adjusting the current out of power source 62, in accordance with the output signal from the controller 42 for the temperature detector, thereby stabilizing the resistivity of the particulates between the electrodes 12a and 12b which are placed on the detecting device for particulate density. Constant voltage is supplied between the electrodes 12a and 12b from the constant voltage power source 61, so that the current flows between both electrodes corresponding to the particulate density attached on the detector. The current is detected by the resistance detector 71, and the detected value is sent to the central controlling unit 7. The central controlling unit 7 determines the timing to refresh the filter from the vehicle conditions such as the detected resistance and temperature, then sends a signal to refresh, into the power source 63 for supplying a power to the heater which refreshes the filter. According to the signal to refresh, the heater 5 to refresh the filter is supplied power so that the filter 3 shown in FIG. 13 is burned to be refreshed. At the same time, the detecting part is refreshed by controlling the current supplied to the electric heating means 22 to heat the detecting part.

In this embodiment, the electric heating means 22 for heating particulates is employed in the detector for particulate density as an electrical heating method, and the electric heating means especially eliminates hydrocarbon and water content from particulates to stabilize the resistivity of the particulates. Thereafter, the influence of the vehicle conditions on the detector for particulate density can be decreased, resulting in less measurement errors. From the particulates around the insulating member 11, are also eliminated hydrocarbon and water content so that the resistivity of the particulates is extremely lowered, such as below 1/1000 and accordingly, the detected resistance becomes much smaller. This can result in the excellent effects that detecting is easy and the errors are very little.

The seventh embodiment of the present invention will be explained hereafter.

Figure 14:
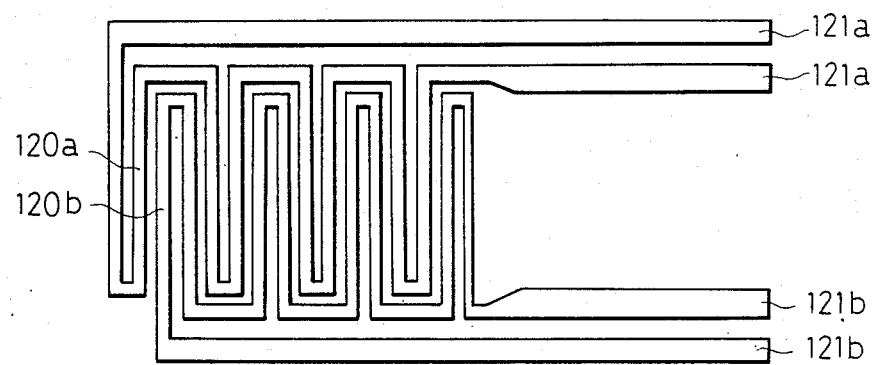
FIG. 14 is a pattern view of the electrode (electric heating means) of the detector for particulate density and FIG. 15 shows a circuit diagram of the controller to refresh a filter utilizing the detector for particulate density.

FIG. 14 shows a pattern for electrodes of the detector for particulate density. A pair of electrodes 120a, 120b are comb shaped and faced to each other. The resistance of the particulates attached on the substrate between the electrodes are detected. The electrode 120a has two lands 121a for connecting lead wires, and the other electrode 120b also has two lands 121b. When the power source is connected between the two lands of the respective electrode, each electrode can be used as a heater. Thus, the electrodes can be used both for an electrode for detecting the resistivity and electric heating means.

Figure 15:
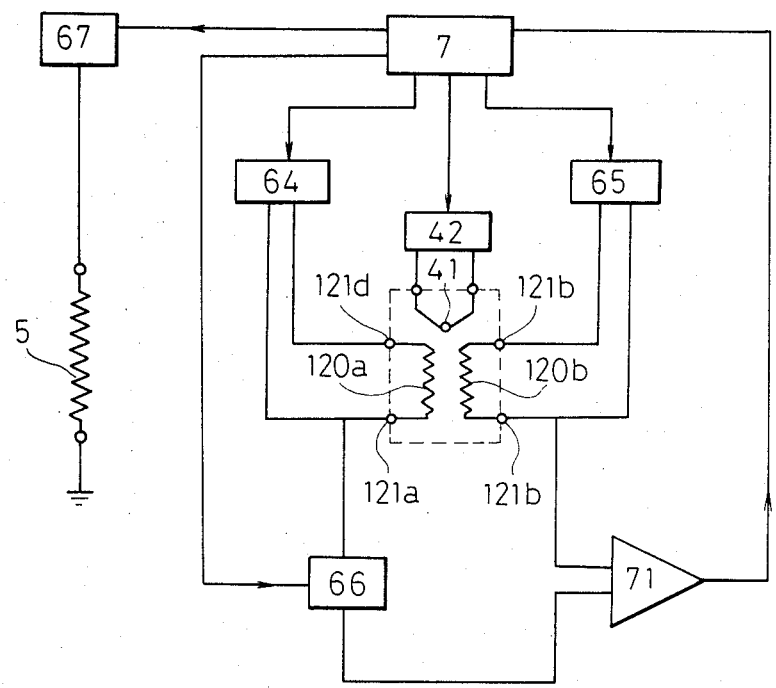

FIG. 15 shows an example of the controller in the equipment for refreshing the filter which employs the detector for particulate density according to the aforesaid seventh embodiment.

The signal output of the temperature detector 41 is sent to the central controlling unit 7, thereafter the central controlling unit 7 sends a signal to the heater controllers 64, 65 so as to control the temperature in the detecting part for particulate density.

The central cntrolling unit 7 controls the heater controllers 64, 65 and the constant voltage power source 66, thereby detecting the resistance of particulates attached between the electrodes 120a and 120b by using both electrodes, and the information of the detected particulate density is transmitted to the central controlling unit 7 via the resistant detector 71. The central controlling unit 7 sends a signal to refresh, to the power source 67 for refreshing the filter when the particulate density comes into the proper refreshing range, thereby the heater 5 for refreshing the filter is supplied power so as to refresh the filter.

In the present embodiment, the electrodes for detecting the resistivity and the electric heating means for heating particulates are simplified so that the heat capacity of the portion to be directly heated is decreased and also the particulates are directly heated. This causes the temperature in the detecting part to be increased more rapidly and thus it can be accurately controlled. Therefore, the present embodiment provides such superior effects that the electric power for heating the particulates attached between the electrodes to stabilize the resistivity can be saved and the measurement errors can be decreased.

As detailed in the foregoing description, the detector for particulate density according to the first feature of the present invention is to detect the density of the conductive particulates attached or absorbed into the heat resistant insulating member, by detecting the resistance variation. And the detector for particulate density is disposed adjacent to the filter so that the density of the particulates trapped within the filter is detected most properly to burn and refresh the filter effectively. Therefore, by the detector according to these embodiments, the particulate density within the filter is detected quite accurately and adequate timing to refresh the filter can be determined.

The second feature of the present invention is the filter including therein the detector for detecting particulate density as in the first feature. Therefore, the particulate density within the filter can be detected directly and extremely accurately, the timing to refresh the filter can be adequately controlled and also the degree of refreshing the filter can be detected.

The third aspect of the present invention is to employ an electric heating means for stabilizing the particulate resistivity by eliminating hydrocarbon and water content. Therefore it has the superior advantage that the particulate density can be detected very precisely.

What is claimed is:

1. A detector for detecting particulate density of engine exhaust gases, comprising:
   a heat resistant insulating member means for trapping conductive particulates, the resistance of said heat resistant insulating member means varying in accordance with the amount of trapped conductive particulates;
   a pair of electrodes disposed opposite to each other in said heat resistant insulating member means, said electrodes being provided for detecting the resistance of said heat resistant insulating member means; and an electric heating means for drying said trapped particulates to allow accurate detection of the resistance of said heat resistant insulating member means.

2. A detector for particulate density according to claim 1, wherein:

said heat resistant insulating member means is cylindrical in shape and is made of ceramics;

said pair of electrodes are comb shaped, projecting portions of one electrode being engaged with those of another one at a space between each other, which are placed on the outer surface of said cylindrical shaped ceramic heat resistant insulating member means; and said electric heating means is disposed on the inner surface of said cylindrical shaped ceramic heat resistant insulating member means.

3. A detector for particulate density according to claim 2, wherein:

each of said electrodes is in a rectangular wave form, with projecting portions of one electrode being engaged with those of another electrode at a space between each.

4. A detector device comprising:

detector means for detecting particulate density of exhaust gases, said detector means comprising;

(a) heat resistant insulating member means for trapping conductive particulates, the resistance of said heat resistant insulating member means varying in accordance with the amount of trapped conductive particulates;

(b) a pair of electrodes disposed opposite to each other in said heat resistant insulating member means, said electrodes being provided for detecting the resistance of said heat resistant insulating member means; and (c) an electric heating means for drying said trapped particulates to allow accurate detection of the resistance of said heat resistant insulating member means;

an insulator connected to said detector means;

a pair of first external terminals disposed in said insulator and extending out of said insulator and connecting to said pair or electrodes;

a pair of second external terminals disposed in said insulator, extending out of said insulator and connecting to said electric heating means; and a housing substantially surrounding said insulator.

5. A controller for regenerating a filter having:

a detector for particulate density comprising;

a heat resistant insulating member for trapping conductive particulates a pair of electrodes disposed opposite to each other in said heat resistant insulating member, for detecting the resistance of said heat resistant insulating member and an electric heating means for drying trapped particulates;

a heater controller for controlling the power supply to said electric heating means, a resistance detector for receiving the signal from said pair of electrodes and detecting the resistance, an ignition heater to burn and regenerate said filter for trapping particulates, a central controlling unit which sends the signal to said heater controller to control turning on or off said electric heating means, and receives the signal from said resistance detector, thereby controlling the timing to turn on or off said ignition heater to regenerate said filter in response to the resistance.

* * * * *